United States Patent [19]
White et al.

[11] Patent Number: 4,829,039
[45] Date of Patent: May 9, 1989

[54] ACTIVATION OF METHANOL/LOW TEMPERATURE SHIFT CATALYSTS USING SOLUBLE ORGANO-METALLIC REDUCING AGENTS

[75] Inventors: James F. White, Macungie; Thomas H. Hsiung, Emmaus, both of Pa.

[73] Assignee: Air Products and Chemicals, Inc., Allentown, Pa.

[21] Appl. No.: 127,854

[22] Filed: Dec. 2, 1987

[51] Int. Cl.$^4$ .................. B01J 31/12; B01J 31/14
[52] U.S. Cl. .................... 502/152; 502/117; 502/154; 502/104
[58] Field of Search ............. 502/117, 152, 154, 104

[56] References Cited

U.S. PATENT DOCUMENTS

Re. 27,845 12/1973 Gilbert et al. ............... 208/89
4,207,249 6/1980 Chauvin et al. ........ 260/449.6 M
4,371,627 2/1983 Chauvin et al. ............ 502/152 X
4,628,065 12/1986 Proteau et al. ............. 502/152 X

FOREIGN PATENT DOCUMENTS 1324534 7/1973 United Kingdom .

Primary Examiner—Patrick P. Garvin
Attorney, Agent, or Firm—Willard Jones, II; James C. Simmons; William F. Marsh

[57] ABSTRACT

The present invention relates to a convenient process for the activation of catalysts, especially copper-zinc catalysts, for use in liquid phase methanol or liquid phase shift reactions, by reduction of the catalyst with soluble organo-metallic reducing agents. The reduction process is fast, can be carried out at atmospheric pressure and low temperature, i.e. less than 100° C., and yields active catalysts with smaller metal crystallite sizes than conventional hydrogen-nitrogen temperature ramping reduction processes.

4 Claims, No Drawings

ACTIVATION OF METHANOL/LOW TEMPERATURE SHIFT CATALYSTS USING SOLUBLE ORGANO-METALLIC REDUCING AGENTS

TECHNICAL FIELD

The present invention relates a process of activation of liquid phase methanol or liquid phase low temperature shift catalysts.

BACKGROUND OF THE INVENTION

U.S. Pat. No. 4,628,065 discloses a processes for methanol synthesis from carbon oxides and hydrogen, performed in an inert liquid medium, in the presence of a catalyst system soluble in the liquid medium. The catalyst system used according to the patent is obtained by reacting a copper compound, optionally associated with a divalent zinc compound and/or a rare earth compound, with a zinc reducing compound.

U.S. Pat. No. 4,371,627 discloses the process for the production of methane by reacting hydrogen with carbon monoxide in the presence of a catalyst manufactured by reacting a nickel compound with a reducing aluminum compound in the presence of a titanium compound. The aluminum compound is preferably a trialkylaluminum compound and the atomic ratio of aluminum to (nickel plus titanium) is preferably from 1:1 to 20:1.

U.S. Pat. No. 4,207,249 discloses a process for the manufacturing of methane also by reacting hydrogen with carbon monoxide in an inert liquid medium comprising a catalyst obtained by reacting a nickel compound with a reducing aluminum compound.

U.S. Pat. No. Re. 27,845 discloses a process for producing a white oil comprising the step of contacting a low sulphur content white oil base stock at hydrogenation conditions with hydrogen and an activated supported transition metal complex catalyst, said catalyst having been prepared by a method comprising contacting a supported transition metal salt with an organo-metallic compound, the metallic compound of which is selected from the Group I, II and III of the periodic table.

SUMMARY OF THE INVENTION

The present invention relates to an improvement to a method for the activation of methanol or low temperature shift catalysts wherein during the activation, one or more metal ions at an initial valance state are reduced from their initial valance state either to a lower valance state or to an elemental state, the improvement comprising contacting said catalysts with at least a stoichiometric quantity of an oil soluble, organo-metallic reducing agent for a period of time sufficient to reduce said metal ions. Examples of organo-metallic reducing agents are diethylzinc, aluminum alkyls, aluminum organo-hydrides, alkali alkyls, alkali organo-hydrides, alkali naphthenides, alkali-aluminum organo-hydrides, alkaline earth alkyls, alkaline earth organo-hydrides, alkaline earth naphthenides, boron alkyls, boron organo-hydrides, and mixtures thereof, wherein the alkyls have one to six carbon atoms.

DETAILED DESCRIPTION OF THE INVENTION

The advent of methanol production utilizing the liquid phase methanol production process has overcome many of the problems of conventional gas phase methanol production. Unfortunately, the standard gas phase activation techniques developed for methanol catalysts used in fixed bed reactors are not well suited for the activation of the finely divided catalysts used in the slurry phase (liquid phase) process. Activation of methanol catalysts typically takes a long time, in addition it requires careful control of the temperature ramping during the activation and very clean hydrogen-nitrogen reduction gas to effectively activate the catalyst. Also, since the reduction (activation reaction) is taking place in three phase slurry system for liquid phase methanol production, gas to liquid mass transfer problems occur if the above careful precautions are not rigidly observed.

Although, in some cases where the slurry concentration is dilute, conventional gas phase reduction procedures can be successfully applied to start-up activation situations, these procedures are tricky in any case and are not easily adaptable for the activation of "makeup" catalyst. "Makeup" catalyst is that catalyst which is added to the liquid phase slurry reactor at appropriate times during normal operation to compensate for catalyst deactivation and to maintain the overall high performance of the process.

The present invention provides a fast, convenient, and simple method of activation of a liquid phase methanol or liquid phase low temperature shift slurry catalyst under mild conditions, i.e. room temperature and ambient pressure, which overcomes the aforementioned problems. The activation method of the present invention is accomplished by the treatment of fresh unactivated catalyst with oil soluble organo-metallic reducing agents such as diethylzinc (DEZ) and triethylaluminum (TEAL). The use of these reducing agents with infinite solubility in the slurry oil avoids mass transfer problems and permits precise control over the concentration of reducing agent. In particular, the method of the present invention may be easily performed without the complexities of normal hydrogen gas based reduction to generate activated slurry phase catalysts.

A typical conventional method of reduction employs the use of either hydrogen or hydrogen/nitrogen mixtures under pressure and a very careful and lengthy temperature ramping scheme; this ramping scheme can last as long as a few days. In contrast, the method of the present invention is carried out at atmospheric pressure and ambient temperature and does not require ramping or careful temperature control for effective activation. Additionally, it is accomplished in a short time, typically, minutes. This shortness of time is due in part to the fact that the reducing agent is soluble and therefore the gas to liquid mass transfer is eliminated.

To carry out the method of catalyst activation by the present invention, a mixture of the oxide catalyst slurried in an inert solvent is treated with an appropriate stoichiometric quantity of the oil soluble, organo-metallic reducing agent, which may be dissolved in the same inert solvent. As stated earlier, the process is carried out at atmospheric pressure, however, it is beneficial for the process to be carried out under an inert gas blanket, i.e. nitrogen. An inert gas blanket is usually required for the handling of metal alkyls and either an inert or reducing atmosphere is required for handling and protecting activated catalyst from damage by air exposure. The order of addition, i.e. adding the catalyst to the reducing agent or the reducing agent to the catalyst, is not believed to be critical, but the addition of the reducing agent to the catalyst should give better control of the activation. The rate of addition is not believed important, however, the rate should be controlled so adequate mixing can occur and any exotherms which may be generated are minimized.

After the addition of the organo-metallic reducing agent to the catalyst slurry and after the completion of the subsequent reduction reaction, the catalyst is ready for use. The activated catalyst can then be heated to the appropriate temperature and used for the desired process reaction, i.e. the methanol production or the shift reactions. Alternatively, if the method is conducted to prepare makeup catalyst for an operating reactor, the activated catalyst may simply be added to the operating reactor by any convenient means.

The ratio of reducing agent to catalyst used in the present method will depend upon several factors. Among them are the following:

The amount and type of metal ion in the catalyst, its valence state, and the desired level of reduction.

The reducing power or reducing equivalent of the organo-metallic reducing agent to be used.

The amount of residual water or other contaminants in the catalyst which may consume the alkyl metal reducing agent in undesirable side reactions.

For example, in the activation of copper oxide-zinc oxide-aluminum oxide methanol catalyst the desired activation step is presumed to be the reduction of copper oxide to copper metal. If diethylzinc were to be used as the organo-metallic reducing agent, and assuming that the reduction converts the diethylzinc substantially to zinc oxide, one mole of diethylzinc should reduce one mole of copper oxide to copper metal. The fate of the alkyl groups is not known, and not believed to be important, although it assumed that they leave as carbon fragments of some sort. If triethylaluminum (TEAL) were to be used for the same copper oxide to copper metal reduction, then one mole of copper oxide requires 2/3 of a mole of triethylaluminum, using the same assumptions as above. More or less, a reducing agent in these ratios would be used depending upon the desired approach to completion of a copper oxide to copper metal reduction and the presence of residual water in the catalyst which may destroy alkali metal compounds by simple hydrolysis.

In another case, for example, an iron oxide-aluminum oxide catalyst the reduction of one mole of $Fe+3$ ion to $Fe+2$ ion (ferric to ferrous) would require ½ mole of diethylzinc or ⅓ mole of triethylaluminum. Similarly, the reduction of one mole of ferric $+3$ ion to iron metal will require 1½ moles of diethylzinc or one mole of triethylaluminum.

The fate of the metallic part of the reducing agent (zinc in the diethylzinc or aluminum in the triethylaluminum) is not precisely known. Although, it is expected that these metallic parts are oxidized and either are inert or become an integral part of the activated catalyst. As such they may act as a selective absorbent or scavenger for catalyst poisons; if so, a beneficial effect may be noted.

It is expected that a wide variety of metal reducing agents such as diethylzinc, aluminum alkyls, aluminum organo-hydrides, alkali metal alkyls, alkali metal hydrides, alkali naphthenides, alkali-aluminum organo-hydrides, alkaline earth alkyls, alkaline earth organo-hydrides, alkaline earth naphthenides, boron alkyls, boron organo-hydrides, and the like, wherein the alkyls have one to six carbon atoms, would be equally effective in the present invention.

To demonstrate the efficacy of the present invention, the following examples are offered:

EXAMPLE 1

Diethylzinc Reduction

In the diethylzinc reduction experiment, 40 grams of a copper oxide/zinc oxide/aluminum commercial methanol catalyst (29.1% copper) was slurried in a 1 liter autoclave under nitrogen at atmospheric pressure and room temperature with 260 grams of Freezene TM 100 oil (Freezene TM 100 oil is a product of Witco Chemical Corporation). To this mixture while stirring was added 25 grams (0.202 moles or 9% excess over a 1:1 stoichiometry) of diethylzinc dissolved in 80 grams of Freezene$^{TM}$ 100 oil. The addition required about three minutes and an exotherm of about 4° C. was noted. The reactor was then heated to 100° C. and then to 200° C. at which time CO-rich syngas, 36.09% hydrogen, 50.6% carbon monoxide, 13.8% carbon dioxide and 0.96% nitrogen, at 750 psig and 10,000 GHSV was introduced. Methanol in the effluent was noticed immediately, but no initial exotherm was apparent, indicating the catalyst had been reduced prior to contact with the syngas. The reaction was run continuously while the temperature was raised to 250° C. At the end of approximately 3½ hours of continuous reaction, a recovery run was made indicating 31.8% hydrogen conversion, 12.95% CO conversion and a methanol productivity of 23.97 millimol/gram of catalyst per hour (mmol/gm-hr). Without optimization, this value is about 92% of the value expected from catalyst activated in a conventional way using 2% hydrogen and 98% nitrogen at 100 psig using a very careful temperature ramping regime requiring in excess of 30 hours to accomplish.

EXAMPLE 2

Triethylaluminum Reduction

A similar experiment to Example 1 was performed using 40 grams of the same copper oxide/zinc oxide/aluminum catalyst slurried in Freezene TM 100 oil and 3.67 grams of triethylaluminum solution received as 50 wt% triethylaluminum in a Isopar E TM (a product of Exxon Corporation) paraffin oil solvent (10% over stoichiometry). The triethylaluminum solution was further diluted with 79.1 grams of Freezene TM 100 oil prior to its addition to the autoclave. No exotherm was noticed. The autoclave was then heated to 100° C. and finally to 224° C. at which time CO-rich syngas (the same as in Example 1) was introduced to the reactor at 750 psig and 10,000 GHSV.

After the CO-rich syngas was introduced the temperature was raised to 250° C. At these conditions methanol was produced at a rate of 9.19 mmol/gm-hr. The temperature was then raised to 300° C. and the resultant methanol production was about 2.83 mmol/gr-hr. In addition to methanol production, dimethylether was also observed to be produced at the 300° C. temperature. When dimethylether is included in the productivity calculation as methanol, since it is the equivalent of 2 moles of methanol, the methanol productivity is increased to 4.61 mmol/gr-hr. A similar observation was made at 325° C. where methanol was made at a rate of 3.95 mmol/gr-hr. These results are lower than expected which is possibly due to the presence of trace chloride in the triethylaluminum. Chloride is a known poison for methanol catalyst.

EXAMPLE 3

Syngas Reduction without Temperature Ramping

A controlled experiment was run in which the same catalyst as in Examples 1 and 2 was subjected an activation procedure with CO-rich syngas, the same as in Examples 1 and 2, at 225°–250° C. without temperature ramping. After the activation was completed and methanol production was started in the autoclave, the results were that there was a methanol productivity at 10,000 GHSV and 246° C. of 16.32 mmol/gr-hr.

As a summary of the different activation procedures of the catalyst and the resultant methanol productivity, the following table is offered.

| Methanol Productivities in Liquid Phase with CO-rich Syngas at 750 psig, 10,000 GHSV, and 250° C. | |
|---|---|
| Reduction Method | Methanol Productivity: mmoles/gm-hr |
| Normal hydrogen nitrogen reduction with ramping at 100 psig | 26.0 |
| Diethyl zinc reduction at room temperature | 23.92 |
| Triethyl aluminum reduction at room temperature | 9.19 |
| Syngas reduction at 225° C. without temperature ramping | 16.3 |
| Syngas reduction with temperature ramping | 26.8 |

From the previous examples, the activation method of the present invention provides a beneficial alternative to the normal lengthy hydrogen-nitrogen reduction type activation procedures. As has been stated, the present invention is the reduction of a metallic ion in a catalyst to either a lower valence state or to the metal. Although the exact chemical mechanism of the reduction by the organo-metallic reducing agent is not precisely known, it is believed that the organ-metallic reacts with the oxide catalysts in such a way to alkalate the catalyst. This would form, in the case of a catalyst containing copper oxide, a copper monoalkyl or dialkyl. Such transition metal alkyls are known to be unstable and decompose to form a hydrocarbon fragment and the reduced metal, i.e., copper in this situation. This schematically would be illustrated as follows using diethyl zinc as the alkali reduction agent.

$$Zn(C_2H_5)_2 + CuO \rightarrow Cu(C_2H_5)_2 + ZnO$$

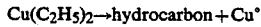

$$Cu(C_2H_5)_2 \rightarrow hydrocarbon + Cu°$$

Other metal alkyls or hydrides would be expected to react in a similar fashion.

As can be seen, the present invention provides a process to activate methanol and low temperature shift production catalysts, especially slurry phase catalysts, quickly at very mild conditions. As such, it represents a method to conveniently and quickly produce active catalysts for either initial start-up or for makeup, thus producing a cost savings in a time sense for initial start-up or resulting in a cost savings both in time and in capital expenditure for makeup.

Additionally, since the activation is conducted at low temperature, it can be postulated that metal crystallite growth in the catalyst should be minimized. The activity of a catalyst is often related inversely to its crystallite size. Crystallite growth is associated with high temperature reduction/activation methods. The table below compares the copper crystallite sizes of used catalysts which were activated by the diethyl zinc procedure of the present invention and a normal hydrogen/nitrogen temperature ramping production.

| | Crystallite Size: Angstroms | |
|---|---|---|
| Activation Procedure | Cu° | ZnO |
| H$_2$/N$_2$ Temperature Ramping | 70–80 | 60–70 |
| Diethylzinc Reduction | 52 | 73 |

The copper crystallite size of 52 Angstroms for the diethylzinc activated catalyst is about 25% smaller than that observed for the hydrogen ramped activated catalyst. Smaller active crystallite sizes are associated with greater catalyst stability and/or activity.

Finally, although the efficacy of the present invention has been demonstrated by use of methanol production examples, the present application is also applicable to shift reaction processes.

The present invention has been described with several specific embodiments thereof. These embodiments should not be viewed as a limitation on the present invention. The limitation of such should be ascertained by the following claims:

We claim:

1. In a method for the activation of finely divided methanol or low temperature shift catalysts wherein during activation of said catalysts one or more metal ions at an initial valance state are reduced from their initial valance state either to a lower valance state or to an elemental state, the improvement comprising contacting said catalysts with at least a stoichiometric quantity of an oil soluble, organo-metallic reducing agent for a period of time sufficient to reduce said metal ions.

2. The method of claim 1 wherein the organo-metallic reducing agent is selected from the group consisting of diethylzinc, aluminum alkyls, aluminum organo-hydrides, alkali alkyls, alkali metal hydrides, alkali naphthenides, alkali-aluminum organo-hydrides, alkaline earth alkyls, alkaline earth organo-hydrides, alkaline earth naphthenides, boron alkyls, boron organo-hydrides, and mixtures thereof and wherein said alkyls have one to six carbon atoms.

3. The method of claim 1 wherein the organo-metallic reducing agent is diethylzinc.

4. The method of claim 2 wherein the aluminum alkyl is triethylaluminum.

* * * * *